(12) United States Patent
Coimbra et al.

(10) Patent No.: US 10,254,296 B2
(45) Date of Patent: Apr. 9, 2019

(54) QUALITATIVE PREDICTIVE METHOD FOR DIFFERENTIAL DIAGNOSIS OF PNEUMOCOCCAL MENINGOCOCCAL AND VIRAL MENINGITIS, METHOD AND KIT FOR DIFFERENTIAL DIAGNOSIS OF MENINGITIS

(71) Applicant: FUNDAÇÃO OSWALDO CRUZ, Rio de Janeiro (BR)

(72) Inventors: Roney Santos Coimbra, Belo Horizonte, MG (BR); Rosiane A da Silva Pereira, Belo Horizonte, MG (BR); Guilherme Correa De Oliveira, Belo Horizonte, MG (BR); Ana Paula Cordeiro, Belo Horizonte, MG (BR)

(73) Assignee: FUNDAÇÃO OSWALDO CRUZ, Rio De Janeiro, RJ (BR)

( * ) Notice: Subject to any disclaimer, the term of this patent is extended or adjusted under 35 U.S.C. 154(b) by 6 days.

(21) Appl. No.: 15/121,869

(22) PCT Filed: Feb. 24, 2015

(86) PCT No.: PCT/BR2015/000021
§ 371 (c)(1),
(2) Date: Aug. 26, 2016

(87) PCT Pub. No.: WO2015/127520
PCT Pub. Date: Sep. 3, 2015

(65) Prior Publication Data
US 2017/0016920 A1    Jan. 19, 2017

(30) Foreign Application Priority Data
Feb. 27, 2014    (BR) .......................... 102014004679

(51) Int. Cl.
| | | |
|---|---|---|
| *A61K 49/00* | (2006.01) | |
| *A61B 5/055* | (2006.01) | |
| *A61K 39/095* | (2006.01) | |
| *G01N 33/68* | (2006.01) | |
| *G01N 33/569* | (2006.01) | |
| *G01N 33/53* | (2006.01) | |
| *G01N 33/92* | (2006.01) | |

(52) U.S. Cl.
CPC ..... *G01N 33/6896* (2013.01); *G01N 33/5308* (2013.01); *G01N 33/56911* (2013.01); *G01N 33/6893* (2013.01); *G01N 33/92* (2013.01); *G01N 2333/4716* (2013.01); *G01N 2333/4737* (2013.01); *G01N 2333/745* (2013.01); *G01N 2333/775* (2013.01); *G01N 2800/28* (2013.01); *G01N 2800/50* (2013.01)

(58) Field of Classification Search
CPC ....... A61K 38/00; A61K 49/085; C07K 14/22
See application file for complete search history.

(56) References Cited

U.S. PATENT DOCUMENTS

| 5,778,895 A | 7/1998 | Barnum et al. |
|---|---|---|
| 2012/0238936 A1* | 9/2012 | Hyde ................. A61B 5/14507 604/8 |
| 2015/0111776 A1* | 4/2015 | Chen ................ G01N 33/54306 506/9 |

FOREIGN PATENT DOCUMENTS

| RU | 2323444 C2 | 4/2008 |
|---|---|---|
| UA | 70047 A | 9/2004 |
| WO | 95/09232 A2 | 4/1995 |

OTHER PUBLICATIONS

Gray et al., The Journal of Pediatrics, 1986; 108(5 part 1): 665-670.*
Philip F. Stahel et al., "Complement C3 and factor B cerebrospinal fluid concentrations in bacterial and aseptic meningitis," The Lancet, Jun. 28, 1997, pp. 1,886-887, vol. 349.
Vitor Laerte Pinto Junior et al., "IL-6 and IL-8 in cerebrospinal fluid from patients with aseptic meningitis and bacterial meningitis: their potential role as a marker for differential diagnosis," Brazilian Journal of Infectious Diseases, Mar. 2011, pp. 156-158, vol. 15, No. 2, Elsevier Editora Ltda.
Hua Song et al., "Apo A-I and apo E concentrations in cerebrospinal fluids of patients with acute meningitis," Annals of Clinical Biochemistry, May 1998, pp. 408-414, vol. 35.
N. Shimetani et al., "Levels of three inflammation markers, C-reactive protein, serum amyloid A protein and procalcitonin, in the serum and cerebrospinal fluid of patients with meningitis," Scandinavian Journal of Clinical and Laboratory Investigation, Sep. 2001, pp. 567-574, vol. 61, No. 7.
Peter R. Donald et al., "Cerebrospinal fluid C-reactive protein in infective meningitis in childhood," Journal of Laboratory and Clinical Medicine, Oct. 1985, pp. 424-427, vol. 106, No. 4.
Philip J. Atkinson et al., "Predominant enteroviral serotypes causing meningitis," Archives of Disease in Children, Apr. 1998, pp. 373-374, vol. 78, No. 4.
E. Bengershôm et al, "Cerebrospinal fluid C-reactive protein in meningitis: diagnostic value and pathophysiology," European Journal of Pediatrics, Sep. 1986, pp. 246-249, vol. 145, Springer-Verlag.
Allan R. Tunkel et al, "Pathogenesis and Pathophysiology of Meningitis," Infectious Disease Clinics of North America, Dec. 1990, pp. 555-581, vol. 4, No. 4.
Anthony S. Fauci, "Infectious Diseases: Considerations for the 21st Century," Clinical Infectious Diseases, Feb. 23, 2001, pp. 675-685, vol. 32, No. 5.

(Continued)

*Primary Examiner* — Gary B Nickol
*Assistant Examiner* — Lakia J Jackson-Tongue
(74) *Attorney, Agent, or Firm* — Piloff & Passino LLP; Sean A. Passino; Rachel K. Pilloff

(57) ABSTRACT

The instant invention relates to a qualitative predictive method, to a method, use and kit applied to the early differential diagnosis of the most prevalent forms of bacterial and viral meningitis, enabling to detect and distinguish the different forms of meningitis. The invention uses a qualitative predictive method based on combined detection and sequential analysis of the presence/absence of at least three out of four specific biomarkers.

7 Claims, 3 Drawing Sheets

(56) References Cited

OTHER PUBLICATIONS

U. R. Goonetilleke et al., "Death Is Associated with Complement C3 Depletion in Cerebrospinal Fluid of Patients with Pneumococcal Meningitis," mBio, Mar. 2012, pp. 1-7, vol. 3, issue 2.

F. Jaeger et al., "Validation of a diagnosis model for differentiating bacterial from viral meningitis in infants and children under 3.5 years of age," European Journal of Clinical Microbiology & Infectious Diseases, Jun. 2000, pp. 418-421, vol. 19, No. 6, Springer-Verlag.

Uwe Koedel et al., "Oxidative Stress in Bacterial Meningitis," Brain Pathology, Jan. 1999, pp. 57-67, vol. 9, No. 1.

Damian N. Meli et al., "Current concepts in the pathogenesis of meningitis caused by *Streptococcus pneumoniae*," Current Opinion in Infectious Diseases, Jun. 2002, pp. 253-257, vol. 15, No. 3, Lippincott Williams & Wilkins.

S. Merkelbach et al., "Cognitive outcome after bacterial meningitis," Acta Neurologica Scandinavica, Aug. 2000, pp. 118-123, vol. 102, No. 2, Munksgaard.

Adriana O. Mukai et al. "TNF-alpha and IL-6 in the diagnosis of bacterial and aseptic meningitis in children," Pediatr Neurol. Jan. 2006, pp. 25-29, vol. 34, No. 1, Elsevier.

Christopher J.L. Murray et al., "The Global Burden of Disease," Aug. 1996, World Health Organization, Harvard University Press.

Barbara Negrini et al., "Cerebrospinal Fluid Findings in Aseptic Versus Bacterial Meningitis," Pediatrics, Feb. 2000, pp. 316-319, vol. 105, No. 2.

Lise E Nigrovic, et al., "Development and validation of a multivariable predictive model to distinguish bacterial from aseptic meningitis in children in the post-Haemophilus influenzae era," Pediatrics, Oct. 2002, pp. 712-719, vol. 110, No. 4.

T.V. Parasuraman et al., "Enteroviral meningitis. Cost of illness and considerations for the economic evaluation of potential therapies," Pharmacoeconomics, Jan. 2001, pp. 3-12, vol. 19, No. 1.

Harish Kumar Pemde et al., "C-Reactive Protein in Childhood Meningitides," The Indian Journal of Pediatrics, Jan. 1996, pp. 73-77, vol. 63, No. 1.

Masatoki Sato et al., "Cytokine and Cellular Inflammatory Sequence in Enteroviral Meningitis," Pediatrics, Nov. 2003, pp. 1,103-1,107, vol. 112, No. 5.

W. Michael Scheld et al., "Pathophysiology of Bacterial Meningitis: Mechanism(s) of Neuronal Injury," Journal of Infectious Diseases, Dec. 1, 2002, pp. S225-S233, vol. 186.

Anne Schuchat et al, "Bacterial Meningitis in the United States in 1995," The New England Journal of Medicine, Oct. 2, 1997, pp. 970-976, vol. 337.

Allan R. Tunkel et al., "Practice Guidelines for the Management of Bacterial Meningitis," Clinical Infectious Diseases, Nov. 1, 2004, pp. 1267-1284, vol. 39, No. 9.

Jorge Alejandro Vázquez et al., "Acute meningitis prognosis using cerebrospinal fluid interleukin-6 levels," The Journal of Emergency Medicine, Aug. 2012, pp. 322-327, vol. 43, No. 2, Elsevier.

International Search Report and Written Opinion for PCT/BR2015/000021, dated May 12, 2015.

\* cited by examiner

QUALITATIVE PREDICTIVE METHOD FOR DIFFERENTIAL DIAGNOSIS OF PNEUMOCOCCAL MENINGOCOCCAL AND VIRAL MENINGITIS, METHOD AND KIT FOR DIFFERENTIAL DIAGNOSIS OF MENINGITIS

This application is a National Stage of International Application no. PCT/BR2015/000021 filed on Feb. 24, 2015, which claims the benefit of Brazil Application no. 102014004679-8 filed on Feb. 27, 2014.

FIELD OF THE INVENTION

The instant invention relates to a qualitative predictive method, to a method and kit applied to the early differential diagnosis of the most prevalent forms of bacterial and viral meningitis, enabling to detect and distinguish the different forms of meningitis. The invention further relates to the use of biomarker proteins for meningitis prediction.

The instant invention uses a qualitative predictive method based on combined detection and sequential analysis of the presence/absence of at least three of four specific biomarkers. Biomarkers are proteins of the inflammatory response of the human host present in patients' cerebrospinal fluid. The application of the qualitative predictive method enables to differentiate patients affected by viral meningitis from the ones affected by bacterial meningitis, also determining the etiology of bacterial meningitis, whether pneumococcal or meningococcal. The instant invention further provides a meningitis differential diagnostic method based on the application of the predictive method and also provides the possibility of incorporating the method of the instant invention into a diagnostic kit containing ligands to biomarker proteins such as antibodies or aptamers, adapted to a laboratory evaluation method that can include ELISA (Enzyme Linked Immunosorbent Assay), chromatography, turbidimetry, capillary electrophoresis, inter alia.

BACKGROUND OF THE INVENTION

Many disease conditions are characterized by differences in levels of gene expression in the presence or concentration of specific proteins and other biomarkers. Within this context, there is the possibility of using predictive models (methods) to aid disease diagnosis.

Meningitis is the inflammation of the meninges in response to infection or exposure to chemical agents. According to the etiology, meningitis are classified as aseptic (AM), with no evidence of causative bacterial infection, or bacterial (BM). While AMs, are mostly are benign and of self-limited course, BMs are associated with high mortality and morbidity that have remained unchanged in the last decades despite the advances in antimicrobial therapy and intensive care aimed at maintaining patients' vital systems (Scheld W, Koedel U, Nathan B, Pfister H: Pathophysiology of bacterial meningitis: mechanism(s) of neuronal injury. J Infect Dis 2002, 186 Suppl 2:S225-233).

Bacterial meningitis (BM) is one of the top ten causes of death related to infections worldwide (Fauci A. Infectious diseases: considerations for the 21st century, Clin Infect Dis 2001, 32(5):675-685), with an estimated incidence of 25/100 thousand cases per year in developed countries, reaching values up to ten times higher in developing countries (Murray J, Lopez A: Global burden of disease and injuries series. Geneva; 1996.). MB is associated with a mortality rate up to 30%. Furthermore, from 30 to 50% of patients who survive the infection develop permanent neurological sequelae, including sensorineural deafness, intellectual disability, learning disabilities, sensory and physical disabilities and cerebral palsy (Merkelbach S, Sittinger H, Schweizer I, Muller M: Cognitive outcome after bacterial meningitis. Acta Neurol Scand 2000, 102(2):118-123).

The most common etiologic agents of MB are *Streptococcus pneumoniae* (pneumococci), *Neisseria meningitidis* (meningococci), and type B *Haemophilus influenzae* (Hib). Since the creation and inclusion of anti-Hib vaccine in the basic vaccination schedule, at the end of the 90s, pneumococci have become the most frequent causative agent of non-epidemic MB acquired in the community among children over one year old (Schuchat A, Robinson K, Wenger J, Harrison L, Farley M, Reingold A, Lefkowitz L, Perkins B. Bacterial meningitis in the United States in 1995. Active Surveillance Team. N Engl J Med 1997, 337(14):970-976). Among BMs, pneumococcal meningitis is the one associated with the highest mortality and morbidity rates. Meningococcal meningitis is mainly an epidemic disease and affects mainly children and young adults.

Aseptic meningitis (AM) is defined as an inflammation of the subarachnoid space, characterized by mononuclear cells pleocytosis and by sterile CSF (cerebrospinal fluid or cerebrospinal fluid) culture. Although the primary cause of AMs are viral infections, AM differential diagnosis includes also tuberculous or fungal meningitis, inflammation caused by parameningeal infection, collagen vascular diseases and meningeal inflammations caused by drug (Ravel R: Clinical Laboratory Medicine: Clinical Application of Laboratory Data: Elsevier Health Sciences; 1994). Viral meningitis are common and often not reported. Non-poliovirus enteroviruses (*Coxsackievirus* and *Echovirus*) are responsible for 80 to 90% of the cases of viral meningitis with determined etiology (Atkinson P, Sharland M, Maguire H: Predominant enteroviral serotypes causing meningitis. Archives of Disease in Childhood 1998, 78:373-374).

BMs are characterized by an intense granulocytic inflammation in the subarachnoid and ventricular spaces, which extends to the perilymphatic space of the inner ear and causes neuronal death, mainly in the cerebral cortex (CX) and hippocampus (HC) and in the cochlear spiral ganglion. In pneumococcal meningitis, cortical areas with morphologic evidence of acute neural necrosis are observed, apoptosis being the predominant form of neuronal damage in the HC (Meli D, Christen S, Leib S, Tauber M: Current concepts in the pathogenesis of meningitis caused by *Streptococcus pneumoniae*. Curr Opin Infect Dis 2002, 15(3):253-257). The inflammatory response to infection determines the BM clinical result. The cascade of inflammatory evens that drives BM pathogenesis is initiated by the presence of the bacteria in the CSF. Bacterial components stimulate the production and release by endothelial cells, astrocytes and microglia, of inflammatory mediators that can directly injure the brain tissue, interact with other modulators of the inflammatory response, or also induce secondary mechanisms capable of causing brain damage (Koedel U, Pfister H: Oxidative stress in bacterial meningitis. Brain Pathol 1999, 9(1):57-67). Another remarkable characteristic of BM is the increased permeability of the blood-brain barrier, which affects homeostasis in the neuronal microenvironment.

Most data on the pathophysiology of MB were obtained from studies using experimental models of pneumococcal meningitis. Little is known about the pathophysiology of meningococcal meningitis. If, on one hand, it is reasonable to formulate some extrapolations from the results of studies focused on the pneumococcal disease, the differences in mortality and morbidity rates between pneumococcal meningitis and meningococcal have remained unexplained.

The inflammatory process observed in patients affected by enterovirus AM is much less well-known than in the case of BM. It is known that the inflammatory response is triggered by the penetration of the virus in the central nervous system (CNS), mainly by hematogenic dissemination from primary infections sites (Tunkel A, Wispelwey B, Scheld W: Pathogenesis and pathophysiology of meningitis. Infect Dis Clin North Am 1990, 4(4):555-581). The presence of the virus in the CNS induces the production/release of proinflammatory cytokines that promote infiltration of leukocytes in the infected area (Sato M, Hosoya M, Honzumi K, Watanabe M, ninomiya N, Shigeta S, Suzuki H: Cytokine and cellular inflammatory response in enteroviral meningitis. Pediatrics 2003, 112(5):1103-1107).

The management of AMs caused by enterovirus is conducted with support therapies for symptom control since there is no drug licensed for clinical use that is effective against these pathogens. In contrast, BM treatment is conducted with antibiotics combined or not with anti-inflammatory drugs. Delays in the administration of antibiotics and anti-inflammatory drugs can have devastating consequences for the patient affected by BM (development of neurosensory sequelae and even death). In case of any suspicion of BM, empiric antibiotic therapy is initiated in order to obtain the results of CSF culture tests.

Thus, the fast differential diagnosis of AM and BM could reduce the hospitalization time of patients affected by AM, treatment costs, patients' exposure to the risk of nosocomial infections, and side effects of antibiotics and anti-inflammatories. Thus, accurate and rapid diagnosis of meningitis is crucial for decision making related to the appropriate therapeutic approach and should be timely for each form of meningitis.

Meningitis Diagnosis

Currently, AM and BM are diagnosed based on clinical and laboratory findings, wherein the CSF examination is essential to confirm the meningitis diagnosis based on clinical signs. The main cytochemical parameters of cerebrospinal fluid currently used in the differential diagnosis of these two types of meningitis are the overall count and differential count of leukocytes, and the levels of total protein and glucose.

These parameters guide the physician's decision to initiate empiric treatment until it has a final diagnosis based on the results of the bacterial culture or of the analysis of pathogen antigens. However, differentiation between BM and AM may be hampered by the variability of the parameters currently used for the diagnosis of these diseases (Negrini B, Kelleher K, Wald E. Cerebrospinal fluid findings in aseptic versus bacterial meningitis. Pediatrics 2000, 105(2):316-319).

Currently, multi-parameter models based on combinations of clinical and laboratory parameters for defining clinical diagnosis of meningitis have been proposed ((Nigrovic L E, Kuppermann N, Malley R. Development and validation of a multivariable predictive model to distinguish bacterial from aseptic meningitis in children in the post-*Haemophilus influenzae* era. Pediatrics. 2002; 110(4):712-9; Jaeger F, Leroy J, Duchene F, Baty V, Baillet S, Estavoyer J M, et al. Validation of a diagnosis model for differentiating bacterial from viral meningitis in infants and children under 3.5 years of age. Eur J Clin Microbiol Infect Dis. 2000; 19(6):418-21). No clinical or laboratory criteria considered alone can differentiate bacterial meningitis from viral meningitis with high sensitivity and good specificity. Thus, several teams have proposed scoring systems that consider combinations of clinical and laboratory parameters to define rules of clinical decision. However, these scoring systems are difficult to transpose between different hospitals and the distribution of the obtained scores appears to be dispersed due to the variability of meningitis clinical presentation.

The identification of meningitis causative agent is fundamental to aid in the choice of the appropriate therapy and in regional epidemiological tracking of the disease. CSF culture is considered the gold standard for the differential diagnosis of meningitis. However, the result of the CSF culture is time-consuming, requiring the use of empiric therapy with broad-spectrum antibiotics, and in some cases, the administration of antibiotics to patients whose etiology proves to be viral shows in the confirmatory diagnosis. Smears of CSF stained by Gram staining and the latex agglutination test are also used as auxiliary methods.

Despite the high specificity, methods for detecting pathogens by molecular biology have their sensitivity affected by antibiotic therapy, can produce false positive results due to remnants of nucleic acids of pathogens present in the cerebrospinal fluid after patient's healing, and hardly apply to hospital laboratories lacking trained staff and adequate infrastructure. In Brazil, such methods have been used only for confirmatory diagnosis and epidemiological studies.

Due to the difficulty in distinguishing patients affected by BM from the one affected by AM during the emergency care, most authors recommend the initiation of antimicrobial therapy in all patients affected by acute meningitis as long as there is any doubt regarding the etiology of the disease until results of CSF bacterial cultures or of antigen identification confirming the pathogen presence are obtained (Tunkel A, Hartman B, Kaplan S, Kaufman B, Roos K, Scheld W, Whitley R: Practice guidelines for the management of bacterial meningitis. Curr Opin Infect Dis 2004, 39(3):1267-1284). If, on one hand, this recommendation allows to treat, in a timely fashion, most cases of BM, it leads to the hospitalization and the use of empiric antibiotics almost systematically, but useless a posteriori, on patients affected by AM (Swingler G, Delport S, Hussey G: An audit of the use of antibiotics in presumed viral meningitis in children. Pediatr Infect Dis J 1994, 13:1107-1110), which increases the risk of nosocomial infections and undesirable effects associated with antibiotic use, and increases considerably the treatment cost (Parasuraman T, Frenia K, Romero J: Enteroviral meningitis. Cost of illness and considerations for the economic evaluation of potential therapies. 2001; 19(1): 3-12). Furthermore, the adjunctive therapy with anti-inflammatory (dexamethasone), as recommended in some BM cases, can aggravate the situation of patients affected by viral meningitis.

The described scenario makes it clear that the fast and accurate differential diagnosis of meningitis is currently a technical demand unmet by the available technological approaches, motivated both by the need to improve the effectiveness of patients' management and by the possibility of reducing the costs of the treatment.

The scientific community has conducted research for identifying new biomarkers for the diagnosis of meningitis, for example, assessing the potential of cytokines and chemokines as markers for differential diagnosis between bacterial and viral meningitis and disease prognosis. However, the evaluation of these biomarkers in their potential diagnosis potential differs between the studies, generating conflicting results. In most studies carried out so far, the concentration of some pro-inflammatory cytokines is considerably increased in the CSF or the serum of patients affected by bacterial meningitis when compared with the ones affected by viral meningitis. However, the evaluation as a diagnostic marker of each cytokine differs between the studies. For example, Vázquez et al. (Vazquez J A, Adducci MeC, Coll C, Godoy Monzón D, Iserson K V. Acute meningitis prognosis using cerebrospinal fluid interleukin-6 levels. J Emerg Med. 2012; 43(2):322-7.) demonstrated that IL-6 is a good marker for the diagnosis and prognosis of bacterial meningitis, wherein concentrations of this interleukin above 35-40 pg/mL would be able to differentiate this disease from viral meningitis or from healthy subjects with 100% sensitivity and 95% specificity. However, other authors concluded that IL-6 should not be used as a marker differential of meningitis due to overlaps of this interleukin concentration ranges in the groups of patients affected by bacterial meningitis, by viral meningitis or without it (Pinto Junior V L, Rebelo M C, Gomes R N, Assis E F, Castro-Faria-Neto H C, Boia M N. IL-6 and IL-8 in cerebrospinal fluid from patients with aseptic meningitis and bacterial meningitis: their potential role as a marker for differential diagnosis. Braz J Infect Dis. 2011; 15(2):156-8, e Mukai A O, Krebs V L, Bertoli C J, Okay T S. TNF-alpha and IL-6 in the diagnosis of bacterial and aseptic meningitis in children. Pediatr Neurol. 2006; 34(1):25-9). For examples, some patients affected by meningococcal meningitis exhibit IL-6 concentrations below 20 pg/mL, while some patients affected by viral meningitis exhibit IL-6 concentrations above 50 pg/mL (Mukai A O et al.). These results contradict the cutoff point proposed by Vazquez and colleagues for the differentiation from cases of bacterial meningitis based on IL-6 dosage.

The diagnostic potential of some biomarkers comprising the qualitative predictive method proposed by the instant invention has been pointed out by the prior art. High concentrations of the complement C3 fraction in the CSF of patients affected by bacterial meningitis were reported when compared with patients affected by viral meningitis and controls without infection in the CNS (Stahel P, Nadal D, Pfister H, Paradisis p, Barnum S. Complement C3 and factor B cerebrospinal fluid concentrations in bacterial and aseptic meningitis. Ther., 89:1231997, 349. 1886-1887; Goonetilleke U, Scarborough M, Ward S, Hussain S, Kadioglu A, Gordon S. Death is associated with complement C3 depletion in cerebrospinal fluid of patients with pneumococcal meningitis. mBio 2012, 3(2): e00272-11). Moreover, U.S. Pat. No. 5,778,895 provides a method for the differential diagnosis of bacterial meningitis based on the measure of the levels of C3 and B fractions of the complement in patients' cerebrospinal fluid.

Several studies further demonstrate the existence of increased levels of C-reactive protein in the CSF and serum of patients affected by bacterial meningitis when compared with patients affected by viral meningitis or control subjects (Nathan B R, Scheld W M. The potential roles of C-reactive protein and procalcitonin concentrations in the serum and cerebrospinal fluid in the diagnosis of bacterial meningitis. Curr Clin Top Infect Dis. 2002; 22:155-65; Donald P R, Strachan A F, Schoeman J F, De Beer F C. Cerebrospinal fluid C-reactive protein in infective meningitis in childhood. J Lab Clin Med. 1985; 106(4):424-7; BenGershom E, Briggeman-Mol G J, de Zegher F. Cerebrospinal fluid C-reactive protein in meningitis: diagnostic value and pathophysiology. Eur J Pediatr. 1986; 145(4):246-9; Pemde H K, Harish K, Thawrani Y P, Shrivastava S, Belapurkar K M. C-reactive protein in childhood meningitides. Indian J Pediatr. 1996; 63(1):73-7).

Furthermore, scientific literature discloses that the concentration of Apolipoprotein A-I in the cerebrospinal fluid of patients affected by meningitis was found to be increased in the acute phase of the disease, returning to basal concentrations in the convalescent phase, while the level of protein in other neurological disorders remained unchanged when compared with the group of control patients (Apo A-I and apo E concentrations in cerebrospinal fluids of patients with acute meningitis. Ann Clin Biochem. 1998 May; 35 (Pt 3):408-14).

However, as observed in the prior art known by the inventors, there is no indication of the use of protein markers to differentiate between forms of the disease. Therefore, the prior art lacks accurate and efficient means for the differential diagnosis of viral, pneumococcal and meningococcal meningitis.

The invention, which will be described in details below, provides a complete and systematic solution for the diagnosis of meningitis and determination of its etiology, in a single test. More specifically, the invention herein discloses a qualitative predictive method based on the combined detection and sequence analysis of the presence/absence of at least three out of four specific biomarkers, capable of differentiating between patients affected by viral meningitis from the ones affected by bacterial meningitis, further determining the etiology of the meningitis, whether it is bacterial, meningococcal or pneumococcal.

SUMMARY OF THE INVENTION

The instant invention relates to a qualitative predictive method, to a method and kit applied to the early differential diagnosis of the most prevalent forms of bacterial and viral meningitis, enabling to detect and distinguish the different forms of meningitis, which is a prerequisite for the timely application of the appropriate therapeutic approach capable of reducing the mortality and morbidity associated with malignant forms of this disease.

In general terms, the methodology of the instant invention employs a qualitative predictive method based on the combined detection and sequence analysis of specific biomarker proteins, represented by the inflammatory response proteins of the human host present in cerebrospinal fluid. The application of the predictive method enables to differentiate patients affected by viral meningitis from the ones affected by bacterial meningitis, also determining the etiology of bacterial meningitis, whether pneumococcal or meningococcal.

The qualitative predictive method was developed on the basis of proteomic studies—by two-dimensional electrophoresis (2D-PAGE) and mass spectrometry (MS)—of the CSF of patients affected by meningitis. The comparison of CSF protein profiles in the groups "viral meningitis", "meningococcal meningitis", "pneumococcal meningitis" and "control" was carried out by analyzing the qualitative differences between these profiles. For each etiology of meningitis and for the group of control subjects the respective intersection subsets—consisting of spots generated by two-dimensional electrophoresis present in all samples of a given group, and union sets—consisting of spots observed in at least one sample of a given group, were formed. The comparison between the intersection subset of the group of patients affected by each studied meningitis etiology with the union set of the group of patients affected by other meningitis etiology or with control subjects resulted in distinctive spots that were found only in the intersection subset of each meningitis etiology. The comparative study was made possible by the composition of a matrix of presence (1) or absence (0) of all the proteins identified by mass spectrometry in each meningitis or control group. In this matrix, proteins were classified as present or absent for each intersection subset and union set of meningitis etiologies or controls. This matrix has ultimately enabled the selection of distinctive proteins that were selected for the composition of the biomarker panel of the qualitative predictive method, namely apolipoprotein A-I, C3 fraction of the complement, C-reactive protein and kininogen.

The qualitative predictive method is based on the combined detection and sequence analysis of the presence/absence of at least three out of the four selected specific biomarkers, capable of differentiating between patients affected by viral meningitis from the ones affected by bacterial meningitis, further determining the etiology of the meningitis, whether it is bacterial, meningococcal or pneumococcal.

The qualitative predictive method consists of three nodes, each one of the nodes being related to the test for detecting at least one out of the four specific protein biomarkers. The first node, represented by the test for the presence of apolipoprotein A-I, allows the distinction between group of patients affected by meningitis from patients without infection in the central nervous system or affected by viral meningitis. The second node of the qualitative predictive method, represented by the test for the presence of C-reactive protein and/or complement C-3 fraction, allows the distinction between the group of patients affected by bacterial meningitis from patients affected by viral meningitis. The third node of the predictive method, represented by the test for the presence of Kininogen, allows the distinction between the group of patients affected by meningococcal meningitis from patients affected by pneumococcal meningitis.

The instant invention further describes a method for the differential diagnosis of meningitis that comprises the detection, by means of immunoassay of biomarkers Apolipoprotein A-I; C-reactive protein and/or complement C-3 fraction in the CSF of patients suspected of having meningitis and sequence analysis of the results, according to the first, second and third nodes of the qualitative predictive method. After the analysis of the third node, the lab technician will be able to determine the diagnosis of meningitis presence and etiology, according to the most prevalent causes: viral meningitis, meningococcal meningitis and pneumococcal meningitis.

The method of the instant invention, based on the combined detection and sequential analysis of the presence/absence of specific biomarkers, can be also incorporated into a diagnostic immonoassay kit containing ligands to biomarker proteins, such as antibodies or aptamers, adapted to a lab evaluation method that can include ELISA (Enzyme Linked Immunosorbent Assay), chromatography, turbidimetry, capillary electrophoresis, inter alia.

Said biomarker protein ligand can be represented by antibodies exhibiting the following characteristics:
  primary antibodies of the IgG or IgM types with specific affinity against epitopes of each of the four biomarkers and produced in rabbits, goats, among other animals; and
  secondary antibodies of the IgG type with specific affinity against epitopes of the heavy chains of IgG or IgM from rabbits, goats or other animals, according to the source and type of the primary antibody used.

The primary and secondary antibodies are conjugated to the enzyme, or biotin or fluorophore. As for signal detection, in the case of enzyme-linked antibody, a substrate that changes color after being modified by the enzyme is used; in the case of biotin-linked antibodies, streptavidin conjugated to the enzyme and the substrate for color production is used; in the case of fluorophore-linked antibodies, detection occurs by light emitted in response to excitation at the appropriate wavelength.

Primary or secondary antibodies coupled to gold or latex particles can also be used for the visual detection of the result.

Alternatively, said ligands to biomarkers proteins may be represented by aptamers, for example, of single stranded DNA oligonucleotides which, in physiological conditions of pH, salinity and temperature, curl assuming three-dimensional conformations presenting a complementary binding sites with tertiary structure regions of each of the four biomarkers. The detection of aptamers bound to biomarkers can be performed on the basis of their capillary electrophoresis migration properties, or biotin or a fluorochrome can be coupled to the aptamers for detection as described above for the antibodies.

Since the instant invention is based on the identification of host immune response proteins rather than pathogen proteins, even in the case of pathogen eradication, the host inflammatory reaction is maintained in the course of the disease, increasing the time window for the differential diagnosis of meningitis through the detection of biomarkers of immune response, which is another advantage associated with the technology. Furthermore, any remnants of nucleic acids of pathogens present in the cerebrospinal fluid after patient's healing, which can cause false positive results in molecular biology methods, do not affect the results of the present invention.

The use of the predictive method, of the method and kit described herein may decisively contribute to the fast diagnosis of the meningitis presence and etiology early in the course of the disease in a patient, allowing to make a conscious decision of the appropriate treatment, avoiding indiscriminate hospitalization and antibiotic therapy, besides reducing treatment costs.

DETAILED DESCRIPTION OF THE INVENTION

Figure 1:
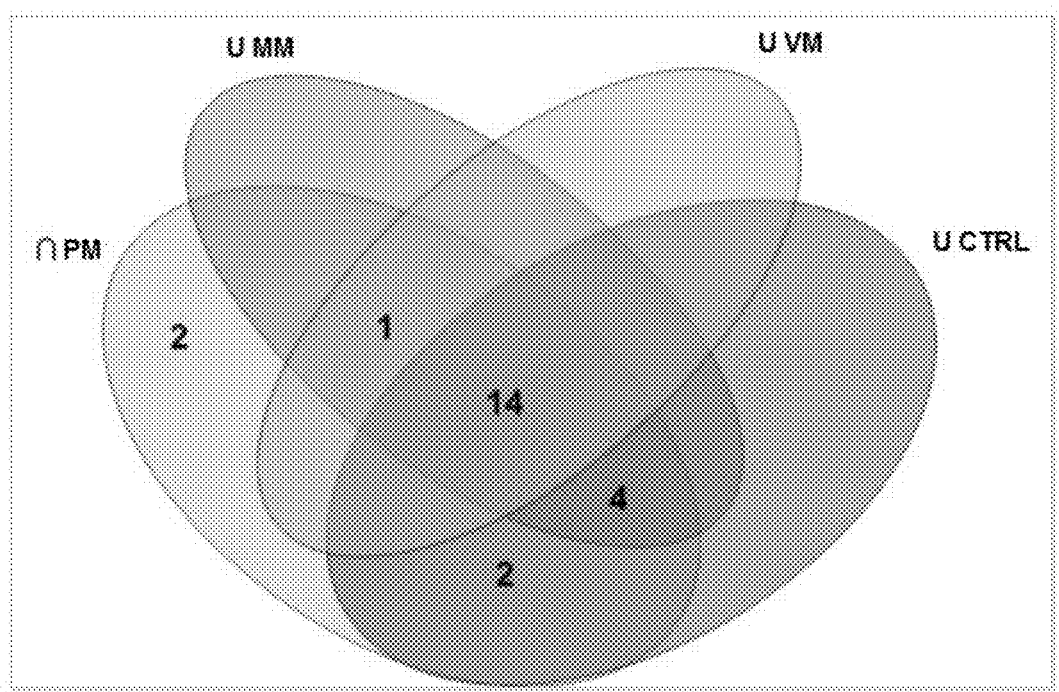
FIG. 1: Venn diagram for the distribution of spots in the interception subset of pneumococcal meningitis. The figure discloses the only two spots of the interception subset of the group of patients affected by pneumococcal meningitis after the comparative analysis between the intersection subset of pneumococcal meningitis and the union sets with other etiologies of meningitis and the control group.

The instant invention relates to a qualitative predictive method, to a method and kit applied to the early differential diagnosis of the most prevalent forms of bacterial and viral meningitis, enabling to detect and distinguish the different forms of meningitis, in the early phase of the disease. In general terms, the methodology of the invention employs a predictive method based on the combined detection and sequence analysis of at least three out of four specific biomarker proteins, represented by the inflammatory response proteins of the human host present in cerebrospinal fluid. The application of the predictive method enables to differentiate patients affected by viral meningitis from the ones affected by bacterial meningitis, also determining the etiology of bacterial meningitis, whether pneumococcal or meningococcal.

The four biomarkers used in the qualitative predictive method include: Apolipoprotein A-I, C-reactive protein, Complement C-3 fraction and Kininogen.

The qualitative predictive method consists of three nodes, each one of the nodes being related to the test of at least one out of the four specific protein biomarkers. The first node, represented by the test for the presence of apolipoprotein A-I, allows the distinction between group of patients affected by meningitis from patients without infection in the central nervous system or affected by viral meningitis. The second node of the qualitative predictive method, represented by the test for the presence of C-reactive protein and/or complement C-3 fraction, allows the distinction between the group of patients affected by bacterial meningitis from patients affected by viral meningitis. The third node of the predictive method, represented by the test for the presence of Kininogen, allows the distinction between the group of patients affected by meningococcal meningitis from patients affected by pneumococcal meningitis.

More specifically, positivity for Apolipoprotein A-I indicates the condition "Meningitis", while the negative result in the first node of the qualitative predictive method indicates "absence of infection into the central nervous system" or "viral meningitis". As for the second qualitative predictive method, positivity for protein of complement C-3 fraction and/or C-reactive protein, combined with the positive result in the first node, indicates the condition "bacterial meningitis"; while negativity for complement C-3 fraction and/or C-reactive protein, combined with positive result in the first node, indicates the presence of viral meningitis. As for the third node of the qualitative predictive method, positivity of kininogen protein, combined with positivity in the first and second nodes, indicates the condition "meningococcal meningitis"; while a negative result in the analysis of the third node, combined with positivity in the first and second nodes, indicates the condition "pneumococcal meningitis".

Therefore, the issuance of the diagnosis about the presence and etiology of meningitis must be based on the following parameters:
(1) Viral meningitis: negative result in the first node of the predictive method, combined with a negative result in the second node of the predictive method; or, positive result in the first node of the predictive method, combined with a negative result in the second node of the predictive method.
(2) Bacterial meningitis, without etiology determination: positive result in the second node of the predictive method, combined with a positive result in the first node of the predictive method.
(3) Meningococcal meningitis: positive result in the third node of the predictive method, combined with a positive result in the first and second nodes of the predictive method.
(4) Pneumococcal meningitis: negative result in the third node of the predictive method, combined with a positive result in the first and second nodes of the predictive method.

The method for the differential diagnosis of meningitis comprises the following steps:
(a) Incubation of the patient's CSF with specific ligands for apolipoprotein A-I; C-reactive protein and/or complement C-3 fraction; kininogen;
(b) Combined detection of apolipoprotein A-I; C-reactive protein and/or complement C-3 fraction; kininogen in the patient's CSF by immunoassay;
(c) Determination of the results using the qualitative predictive method, by means of sequential analysis of the first, second and third nodes, wherein:
  (i) a negative result in the first node of the predictive method combined with a negative result in the second node of the predictive method; or, positive result in the first node of the predictive method combined with a negative result in the second node of the predictive method indicates the condition "viral meningitis";
  (ii) a positive result in the second node of the predictive method combined with a positive result in the first node of the predictive method indicates the condition of "bacterial meningitis";
  (iii) a positive result in the third node of the predictive method combined with a positive result in the first and second nodes of the predictive method indicates the condition of "meningococcal meningitis".
  (iv) a negative result in the third node of the predictive method combined with a positive result in the first and second nodes of the predictive method indicates the condition of "pneumococcal meningitis".

The method of the instant invention, based on the combined detection and sequential analysis of the presence/absence of specific biomarkers, can be incorporated into a diagnostic immonoassay kit containing ligands to biomarker proteins, such as antibodies or aptamers, adapted to an lab evaluation method that can include ELISA (Enzyme Linked Immunosorbent Assay), chromatography, turbidimetry, capillary electrophoresis, inter alia.

In order to achieve and understand in details the subject matter in which the aforementioned characteristics, advantages and objectives of the invention, as well as other ones that will become clear, more particular descriptions of the invention are illustrated in the following Examples. However, the Examples illustrate preferred embodiments of the invention and, thus, should not be considered limiting in their scope.

Example 1

Casuistry

For the comparative analysis of the CSF proteome through two-dimensional gels, 18 patients affected by pneumococcal meningitis, meningococcal meningitis or viral meningitis and six control individuals were selected (Table 1), all undergoing CSF lumbar puncture. Immediately after CSF collection, the samples were centrifuged for cell separation and supernatants were frozen at −20° C., and subsequently at −80° C. until analyzed.

TABLE 1

CHARACTERIZATION OF THE POPULATION UNDER STUDY

| | SOCIO-DEMOGRAPHICAL DATA | | | | LABORATORY CLINICAL DATA | | | | | | | | |
|---|---|---|---|---|---|---|---|---|---|---|---|---|---|
| Patients | Age | Gender | H. IJPII | H. GT | Clinical sign | Fever | Meningeal signs | Leukocytes | % PMN | Proteins | Glucose | Culture | Gram | Latex |
| PM | | | | | | | | | | | | | | |
| 1 | 9 y | M | x | | vomit | (+) | (+) | 5,600 | 80 | 441 | 71 | (+) | N/A | N/A |
| 2 | 22 y | M | | x | N/A | N/A | N/A | 1,438 | 90 | 185 | 26 | N/A | (+) | N/A |
| 3 | 13 y | M | | x | N/A | N/A | N/A | 4,400 | 93 | 186 | 20 | (+) | (+) | (+) |
| 4 | 23 y | M | | x | N/A | N/A | N/A | 645 | 95 | 335 | 2.5 | (+) | (+) | N/A |
| 5 | 36 y | M | | x | N/A | N/A | N/A | 960 | 87 | 474 | 1.5 | (+) | (+) | N/A |
| 6 | 2 y | F | x | | vomit; headache | (+) | (+) | 240 | 92 | 110 | 1 | (+) | (+) | (+) |
| MM | | | | | | | | | | | | | | |
| 1 | 13 y | F | x | | vomit | (+) | (+) | 72 | 5 | 66 | 41 | N/A | (+) | N/A |
| 2 | 5 m | F | x | | vomit | (+) | (+) | 2,560 | 44 | 187 | 3 | (+) | (+) | (+) |
| 3 | 12 y | F | x | | vomit | (+) | (+) | 19,500 | 96 | 461 | 0 | (+) | N/A | N/A |
| 4 | 5 y | M | x | | vomit | (+) | (+) | 6,800 | 95 | 202 | 53 | N/A | N/A | (+) |
| 5 | 8 y | F | | x | N/A | N/A | N/A | 13,500 | 94 | 80 | 2 | (−) | (+) | (−) |
| 6 | 11 y | F | x | | vomit | (+) | (+) | 120 | 94 | 281 | 48 | (+) | (+) | N/A |
| VM | | | | | | | | | | | | | | |
| 1 | 4 y | F | x | | vomit | (+) | (+) | 500 | 30 | 31 | 49 | N/A | (−) | (−) |
| 2 | 4 y | M | x | | (−) | (+) | (−) | 2 | 8 | 18 | 51 | N/A | (−) | (−) |
| 3 | 6 y | F | x | | vomit; headache | (+) | (+) | 44 | 56 | 36 | 43 | (−) | (−) | (−) |
| 4 | 8 y | M | x | | vomit; headache | (+) | (+) | 33 | 73 | 38 | 50 | N/A | (−) | (−) |
| 5 | 3 y | M | x | | malaise | (−) | (+) | 53 | 10 | 29 | 47 | N/A | N/A | (−) |
| 6 | 11 m | F | x | | vomit | (+) | N/A | 21 | 60 | 32 | 57 | (−) | (−) | N/A |
| CTRL | | | | | | | | | | | | | | |
| 1 | 7 y | M | x | | vomit | (+) | (+) | 6 | 54 | 35 | 72 | N/A | N/A | N/A |
| 2 | 3 y | M | x | | malaise | (+) | (−) | 9 | 94 | 20 | 50 | N/A | N/A | N/A |
| 3 | 33 y | M | | x | N/A | N/A | N/A | 2 | 80 | 30 | 40 | (−) | N/A | N/A |
| 4 | 2 y | M | x | | (−) | (−) | N/A | 2 | 13 | 21 | 62 | N/A | N/A | N/A |
| 5 | 11 m | F | x | | vomit | (+) | (−) | 1 | 7 | 26 | 58 | (−) | (−) | N/A |
| 6 | 5 m | F | x | | (−) | (+) | N/A | 2 | 0 | 24 | 51 | (−) | (−) | N/A |

Where:
PM Pneumococcal meningitis;
MM: Meningococcal meningitis;
VM: Viral meningitis;
CTRL: Control;
H. IJPII: Hospital Infantil Joao Paulo II;
H.GT: Hospital Giselda Trigueiro;
y: years;
m: months;
M: male;
F: female;
(+): positive;
(−): negative;
N/A: ignored;
Gram: Gram bacterioscopy;
Leukocytes (cells/mm3);
Proteins and Glucose: mg/dL;
culture data, Gram and latex: in the CSF.

Moreover, the results of the CSF cytochemical parameter tests were analyzed, namely: total and differential leukocyte count, total proteins and glucose of the group of patients constituting this study for comparison with data pre-established in the scientific literature. The results of these tests were collected from the review of the patients' medical records.

The confirmatory diagnosis of bacterial meningitis is made by detecting pathogens in CSF, or blood, through one or more of the following tests: culture, Gram bacterioscopy or latex agglutination. The diagnosis of viral meningitis was conducted by exclusion of the bacterial forms of meningitis when there was a clinical condition of meningitis with negative results for the culture, Gram bacterioscopy and latex agglutination, but with a leukocyte count slightly higher (>50 cells), wherein protein levels may be slightly higher or normal (normal: 15 to 45 mg/dL) and glucose levels may be normal or slightly lower (normal: 60 mg/dL). The control group consisted of subjects without CNS infection, systemic infections, psychiatric or neurodegenerative diseases checked for suspected meningitis, but whose disease was discarded by confirmatory diagnosis and by normal cytochemical parameter values.

The evaluation of the total leukocyte count parameter showed significant differences between patients affected by bacterial meningitis compared with those affected by viral meningitis or controls and between the latter two. Median values of leukocyte count found in the CSF in patients affected by pneumococcal meningitis (PM) and meningococcal meningitis (MM) (PM: 1,199 cells/mm3 and MM: 4,680 cells/mm3) were significantly higher than the ones found in patients affected by viral meningitis (VM) and controls (CTRL) (VM: 44.5 cells/mm3 and CTRL: 2 cells/mm3). However, overlaps of the leukocyte values were observed, for example, among patients affected by meningococcal meningitis and viral meningitis, which makes it impossible to discriminate between these patients.

Protein concentration in the CSF is considered one of the most sensitive indicators of pathology in the CNS. The results demonstrate significant differences between patients affected by bacterial meningitis (PM: 260.5 mg/dL and MM: 194.5 mg/dL) when compared with the ones affected by viral meningitis (VM: 31.5 mg/dL) or controls (CTRL: 25 mg/dL) ($p<0.01$), but not between the two latter, given that both show protein concentration values within the normal values (18 to 58 mg/dL). Although the total protein levels in CSF of normal subjects are slightly different from the ones observed in patients affected by viral meningitis, the median value of the latter is within the range considered normal. Moreover, overlaps of total protein values were observed among patients affected by pneumococcal meningitis and meningococcal meningitis, which makes it impossible to discriminate between these patients.

The analyses conducted for the differential count parameters of polymorphonuclear leukocytes (PMN) and total glucose in the CSF revealed no statistically significant difference between the groups under study. Median values found for leukocyte differential count of PMN leukocytes in patients affected by bacterial meningitis (PM: 91% and MM: 94%) were higher than the ones found in patients affected by viral meningitis (VM: 43%) and controls (CTRL: 54%), but the differences were not statistically significant ($p>0.05$). Median values for CSF glucose found for patients affected by pneumococcal meningitis (22.5 mg/dL) were lower than the ones found for patients affected by meningococcal meningitis (41 mg/dL). All the patients affected by viral meningitis and the controls exhibit glucose concentrations within normal values (>40 mg/dL).

Thus, in this small sample none of the classic cytochemical parameters, when analyzed separately, proved to be sufficiently sensitive and specific for the differential diagnosis of pneumococcal, meningococcal or viral meningitis.

Example 2

Sample Processing

CSF contains small molecules, salts, peptides, proteins and enzymes that play critical roles in many physiological processes. In order to improve the resolution of two-dimensional electrophoresis most of the salt content of the CSF must be removed to eliminate possible interferences.

CSF samples in raw state from patients affected by viral meningitis and controls exhibited a much lower protein concentration when compared with the protein concentrations of CSF samples from patients affected by bacterial meningitis. It is important to stress that more than 15% of the total protein content of the CSF corresponds to albumin and 15% or more, to immunoglobulins. Therefore, depletion of abundant proteins is essential to detect less representative proteins in the CSF. In order to obtain a sufficient amount of protein for the subsequent steps of the method of the instant invention, twice the volume of CSF in the raw state was used for samples from patients affected by viral meningitis and controls compared with patients affected by bacterial meningitis.

Six samples of each etiology (pneumococcal, meningococcal or viral meningitis) and six samples of control subjects were concentrated from 30 to 35 times for bacterial samples, from 40 to 45 times for viral samples and controls by acetone precipitation. Albumin and immunoglobulins were depleted using columns prepared with a mixture of anti-HSA Sepharose and protein G Sepharose of high performance. Then, the proteins were precipitated again with acetone for concentration and desalting. In this step, all the samples were concentrated of approximately 20 times. Precipitates were resuspended in a rehydration buffer (IEF) and protein concentrations were determined by Bradford method in a raw state and, after depletion, using standard with bovine serum albumin. In order to verify the quality of the samples in raw state and verify the efficiency of albumin and IgG depletion, the samples were separated by unidimensional electrophoresis in 12% polyacrylamide denaturing gel (SDS-PAGE) and dyed with silver nitrate.

Example 3

Protein Separation by Two-Dimensional Electrophoresis

Twelve two-dimensional gels containing 0.5 μg of CSF proteins (representing samples from six subjects and their technical duplicates) and control group were manufactured for each of meningitis etiology under study, for a total of 48 gels. The fixed amount of 0.5 μg protein was prepared for isoelectric focusing using 7 cm-IPG strips, pH 3-10NL in PROTEAN IEF Cell equipment (BioRad, PA, USA) at 20° C., 50 mA/gel under the conditions described below: passive rehydration for 4 hours, 20° C.; Step 1: 50 V, 12 hours; Step 2: 500 V, 30 minutes; Step 3: 1,000 V, 30 minutes; Step 4: 4,000 V, 1 hour; and Step 5: 4,000 V, 16,000 V-hr. After conducting the equilibration steps (reduction and alkylation of proteins), the strips were subjected to the process of protein separation by the second dimension, conducted through PAGE in a 12% polyacrylamide gel, and the gels were dyed with silver nitrate.

2DE gel images of patients' samples constituting the group of pneumococcal, meningococcal and viral meningitis and controls were analyzed by the software PDQuest 7.3.0 (Bio-Rad, PA, EUA). The scanned images of the two-dimensional gels were used for qualitative analysis of the CSF proteome, that is, the comparison between CSF protein profiles from patients with pneumococcal meningitis, meningococcal meningitis and viral meningitis, and the comparison between these and the protein profiles obtained from CSF of control subjects.

For each meningitis etiology and for the group of control subjects the respective intersection subsets—consisting of spots present in all the 12 two-dimensional gels containing the samples from the six subjects of a given group, and union sets—consisting of the spots observed in at least one out of the 12 two-dimensional gels with samples from the six subjects of each group, as shown in Table 2.

TABLE 2

NUMBER OF SPOTS THAT FORM INTERCEPTION SUBSETS AND UNION SETS OF THE CSF OF PATIENTS AFFECTED BY MENINGITIS AND CONTROLS

|  | PM | MM | VM | CTRL |
|---|---|---|---|---|
| Union (U) | 170 | 105 | 75 | 121 |
| Interception (∩) | 23 | 33 | 27 | 17 |

Where:
PM: pneumococcal meningitis;
MM: meningococcal meningitis;
VM: viral meningitis;
CTRL: control.

The comparison between the intersection subset of the group of patients affected by each studied meningitis etiology with the union set of the group of patients affected by other meningitis etiology or with control subjects resulted in distinctive spots that were found only in the intersection subset of each meningitis etiology (Table 3).

The results of the comparative analyses between the spots of the interception subset of patients affected by pneumococcal meningitis and the spots of the union sets of the control groups and of other meningitis etiology resulted in single spot of intersection subset of patients affected by pneumococcal meningitis, as shown in FIG. 1. Only two spots of the interception subset of the group of patients affected by pneumococcal meningitis were found after the comparative analysis between the intersection subset of pneumococcal meningitis and the union sets with other etiologies of meningitis and the control group.

Figure 2:
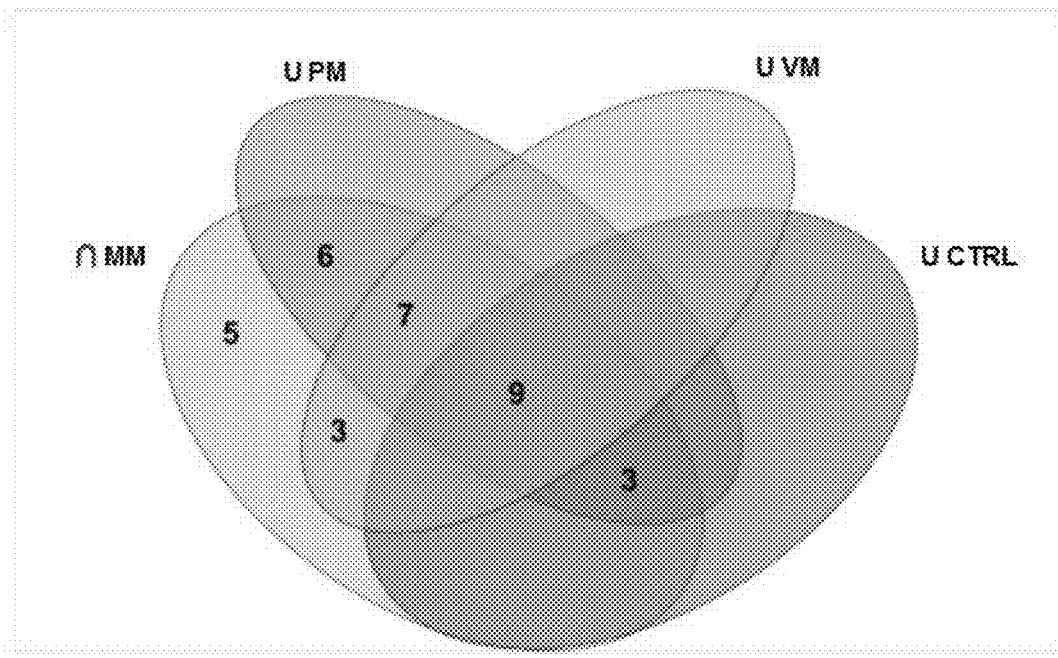
FIG. 2: Venn diagram for the distribution of spots in the interception subset of meningococcal meningitis. The figure discloses the only five spots of the interception subset of the group of patients affected by meningococcal meningitis after the comparative analysis between the intersection subset of meningococcal meningitis and the union sets with other etiologies of meningitis and the control group.

The results of the comparative analyses between the spots of the interception subset of patients affected by meningococcal meningitis and the spots of the union sets of the control groups and of other meningitis etiology resulted in single spot of intersection subset of patients affected by meningococcal meningitis, as shown in FIG. 2. Five single spots of the interception subset of the group of patients affected by meningococcal meningitis were found after the comparative analysis between the intersection subset of meningococcal meningitis and the union sets with other etiologies of meningitis and the control group.

Figure 3:
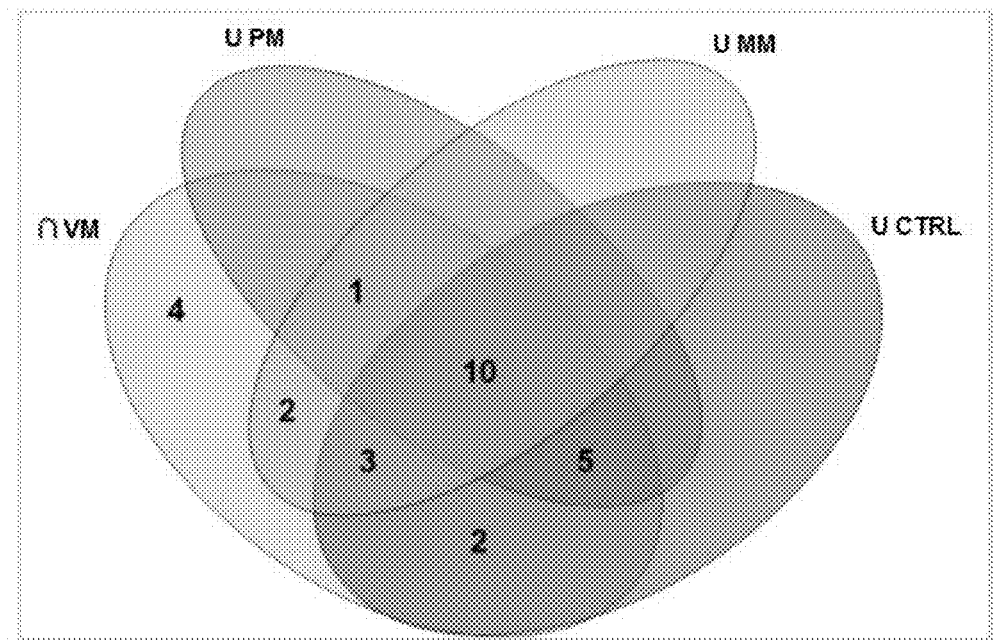
FIG. 3: Venn diagram for the distribution of spots in the interception subset of viral meningitis. The figure discloses the only four spots of the interception subset of the group of patients affected by viral meningitis after the comparative analysis between the intersection subset of viral meningitis and the union sets with other etiologies of meningitis and the control group.

The results of the comparative analyses between the spots of the interception subset of patients affected by viral meningitis and the spots of the union sets of the control groups and of other meningitis etiology resulted in single spot of intersection subset of patients affected by viral meningitis, as shown in FIG. 3. Four single spots of the interception subset of the group of patients affected by viral meningitis were found after the comparative analysis between the intersection subset of viral meningitis and the union sets with other etiologies of meningitis and the control group.

Thus, the single spots found in the intersection subsets of each meningitis etiology were prioritized for mass spectrometry identification for subsequent qualitative composition of the meningitis predictive method.

Example 4

Identification of Differentially Expressed Proteins by Mass Spectrometry

The comparative analysis of the two-dimensional gels with CSF proteins of patients affected by meningitis and

TABLE 3

SPOTS DEFINED IN THE COMPARATIVE ANALYSIS BETWEEN THE DIFFERENT MENINGITIS ETIOLOGIES AND THE CONTROL GROUP

| | UNION SETS | | | | | | | |
|---|---|---|---|---|---|---|---|---|
| | CTRL (121 spots) | | PM (170 spots) | | MM (105 spots) | | VM (75 spots) | |
| | INTERCEPTION SUBSETS | | | | | | | |
| | Common | Distinctive | Common | Distinctive | Common | Distinctive | Common | Distinctive |
| PM (23 spots) | 20 | 3 | — | — | 19 | 4 | 15 | 8 |
| MM (33 spots) | 12 | 21 | 24 | 9 | — | — | 19 | 14 |
| VM (27 spots) | 20 | 7 | 16 | 11 | 16 | 11 | — | — |

Where:
PM: pneumococcal meningitis;
MM: meningococcal meningitis;
VM: viral meningitis;
CTRL: control.

controls allowed the selection of the protein spots corresponding to potential biomarkers for each meningitis etiology.

Two-dimensional gels were prepared using pools of three samples from patients affected by pneumococcal meningitis and meningococcal meningitis, or viral meningitis, respectively. For each meningitis etiology, three two-dimensional gels of samples containing 10, 40 and 100 μg of the protein were prepared in order to increase the probability of success in the identification of distinct proteins with possible overlaps in the proteomic map. All the proteins identified in each produced gel were considered in the instant invention. In this step, gels were dyed by colloidal Coomassie compatible with mass spectrometry.

Out of the 695 protein spots submitted to mass spectrometry, 553 (80%) were identified and correspond to 131 different protein. Of these, 37 proteins correspond to spots belonging to the interception subset of pneumococcal, meningococcal or viral meningitis. In addition to the spots belonging to the intersection subsets of the group of patients affected by meningitis and absent in the union set of other etiologies of the disease or control subjects, all spots of the union sets of each meningitis etiology were sought to be identified.

Most of single spots of the interception subsets of each meningitis etiology was discharged as potential biomarker, after identification by mass spectrometry, for being spots whose identified protein was also found in other spots of the two-dimensional gels. The same protein may be present in more than one spot, possibly due to the occurrence of post-translational modifications, such as carbonylation, phosphorylation and methylation, and in vivo proteolysis, via proteasome and lysosome.

A matrix of presence (1) or absence (0) consisting of the list of all the proteins corresponding to the intersection spots belonging to the interception subsets identified by mass spectrometry was built (Table 4, Table 5 and Table 6). In this matrix, proteins were classified as present or absent for each intersection subset and union set of meningitis etiologies or controls. Therefore, this matrix allowed the selection of the five spots, that, together with the only two spots belonging to the subset intersection of meningococcal meningitis, correspond to the four proteins used to build the qualitative predictive method for meningitis diagnosis.

TABLE 4

MATRIX OF THE SPOTS OF THE INTERCEPTION SUBSETS OF THE GROUP OF PATIENTS AFFECTED BY PNEUMOCOCCAL MENINGITIS

| | | Spots | | | | | | Reviewed after protein identification | | | | |
|---|---|---|---|---|---|---|---|---|---|---|---|---|
| | | | | U | | | | | | | | |
| Spot | Proteins | ∩ MM | ∩ VM | U MM | U VM | U Ctrl | gi | ∩ MM | ∩ VM | U MM | U VM | U Ctrl |
| p.1 | α-2-HS-glycoprotein | 0 | 0 | 0 | 0 | 1 | 112910 | 0 | 0 | 1 | 1 | 1 |
| p.2 | α-1-antitrypsin | 0 | 0 | 0 | 0 | 1 | 6137432 | 1 | 1 | 1 | 1 | 1 |
| p.3 | α-1-antitrypsin | 0 | 0 | 1 | 1 | 1 | 6137432 | 1 | 1 | 1 | 1 | 1 |
| p.4 | α-1-antitrypsin | 0 | 0 | 1 | 1 | 1 | 6137432 | 1 | 1 | 1 | 1 | 1 |
| p.5 | α-1-antitrypsin | 0 | 0 | 0 | 0 | 0 | 6137432 | 1 | 1 | 1 | 1 | 1 |
| p.6 | α-1-HS-glycoprotein | 1 | 0 | 1 | 1 | 1 | 223069 | 1 | 0 | 1 | 0 | 1 |
| p.7 | α-1-antitrypsin | 0 | 0 | 1 | 1 | 1 | 6137432 | 1 | 1 | 1 | 1 | 1 |
| p.8 | Hemopexin | 0 | 0 | 1 | 1 | 1 | 386789 | 1 | 1 | 1 | 1 | 1 |
| p.9 | Hemopexin | 0 | 0 | 1 | 1 | 1 | 386789 | 1 | 1 | 1 | 1 | 1 |
| p.10 | Hemopexin | 0 | 0 | 1 | 1 | 1 | 386789 | 1 | 1 | 1 | 1 | 1 |
| p.11 | Albumin | 0 | 0 | 1 | 1 | 1 | 28592 | 1 | 0 | 1 | 1 | 1 |
| p.12 | not identified | 0 | 0 | 1 | 1 | 1 | — | 0 | 0 | 1 | 1 | 1 |
| p.13 | Transferrin | 0 | 0 | 1 | 1 | 1 | 115394517 | 1 | 1 | 1 | 1 | 1 |
| p.14 | Transferrin | 0 | 0 | 1 | 1 | 1 | 115394517 | 1 | 1 | 1 | 1 | 1 |
| p.15 | Transferrin | 0 | 0 | 1 | 1 | 1 | 115394517 | 1 | 1 | 1 | 1 | 1 |
| p.16 | C3 Component | 1 | 0 | 1 | 0 | 1 | 179665 | 1 | 0 | 1 | 0 | 1 |
| p.17 | Haptoglobin | 0 | 0 | 1 | 1 | 1 | 306882 | 1 | 0 | 1 | 1 | 1 |
| p.18 | Haptoglobin | 0 | 0 | 1 | 1 | 1 | 306882 | 1 | 0 | 1 | 1 | 1 |
| p.19 | Haptoglobin | 0 | 0 | 1 | 1 | 1 | 306882 | 1 | 0 | 1 | 1 | 1 |
| p.20 | C-reactive | 1 | 0 | 1 | 0 | 1 | 1942435 | 1 | 0 | 1 | 0 | 1 |
| p.21 | Apolipoprotein AI | 1 | 0 | 1 | 1 | 0 | 90108664 | 1 | 0 | 1 | 1 | 0 |
| p.22 | Transthyretin | 1 | 0 | 1 | 0 | 1 | 17942890 | 1 | 1 | 1 | 1 | 1 |
| p.23 | Transthyretin | 0 | 0 | 0 | 0 | 0 | 17942890 | 1 | 1 | 1 | 1 | 1 |

Where:
∩: interception subset;
U: union set;
MM: meningococcal meningitis;
VM: viral meningitis;
Ctrl: control.

TABLE 5

MATRIX OF THE SPOTS OF THE INTERCEPTION SUBSETS OF THE GROUP OF PATIENTS AFFECTED BY MENINGOCOCCAL MENINGITIS

| | | Spots | | | | | | Reviewed after protein identification | | | | |
|---|---|---|---|---|---|---|---|---|---|---|---|---|
| Spot | Proteins | ∩ PM | ∩ VM | U PM | U VM | U Ctrl | gi | ∩ PM | ∩ VM | U PM | U VM | U Ctrl |
| m.1 | Ceruloplasmin | 0 | 0 | 1 | 0 | 1 | 1620909 | 0 | 0 | 0 | 1 | 1 |
| m.2 | α-1-B-Glycoprotein | 0 | 0 | 1 | 0 | 0 | 69990 | 0 | 0 | 1 | 1 | 1 |

TABLE 5-continued

MATRIX OF THE SPOTS OF THE INTERCEPTION SUBSETS OF THE GROUP OF PATIENTS AFFECTED BY MENINGOCOCCAL MENINGITIS

| | | Spots | | | | | | Reviewed after protein identification | | | | |
|---|---|---|---|---|---|---|---|---|---|---|---|---|
| Spot | Proteins | ∩ PM | ∩ VM | U PM | U VM | U Ctrl | gi | ∩ PM | ∩ VM | U PM | U VM | U Ctrl |
| m.3 | α-1-B-Glycoprotein | 0 | 0 | 1 | 1 | 1 | 69990 | 0 | 0 | 1 | 1 | 1 |
| m.4 | chain β T cell receptor | 0 | 0 | 1 | 0 | 0 | 78101492 | 0 | 0 | 1 | 1 | 0 |
| m.5 | Hemopexin | 0 | 0 | 1 | 0 | 1 | 386789 | 1 | 1 | 1 | 1 | 1 |
| m.6 | Hemopexin | 0 | 0 | 1 | 1 | 1 | 386789 | 1 | 1 | 1 | 1 | 1 |
| m.7 | Hemopexin | 0 | 0 | 0 | 1 | 1 | 386789 | 1 | 1 | 1 | 1 | 1 |
| m.8 | Hemopexin | 0 | 0 | 1 | 1 | 1 | 386789 | 1 | 1 | 1 | 1 | 1 |
| m.9 | Chain β T cell receptor | 1 | 1 | 1 | 1 | 0 | 78101492 | 1 | 1 | 1 | 1 | 0 |
| m.10 | Transferrin | 1 | 1 | 1 | 1 | 1 | 115394517 | 1 | 1 | 1 | 1 | 1 |
| m.11 | Transferrin | 1 | 1 | 1 | 1 | 0 | 115394517 | 1 | 1 | 1 | 1 | 1 |
| m.12 | Transferrin | 1 | 1 | 1 | 1 | 1 | 115394517 | 1 | 1 | 1 | 1 | 1 |
| m.13 | Transferrin | 1 | 1 | 1 | 1 | 1 | 115394517 | 1 | 1 | 1 | 1 | 1 |
| m.14 | Transferrin | 1 | 0 | 1 | 0 | 0 | 115394517 | 1 | 1 | 1 | 1 | 1 |
| m.15 | α-1-antichymotrypsin | 1 | 0 | 1 | 0 | 1 | 177933 | 1 | 0 | 1 | 0 | 1 |
| m.16 | α-1-antitrypsin | 1 | 1 | 1 | 1 | 0 | 6137432 | 1 | 1 | 1 | 1 | 1 |
| m.17 | Kininogen | 0 | 0 | 0 | 0 | 0 | 4504893 | 0 | 0 | 0 | 0 | 0 |
| m.18 | Vitamin D binding protein | 1 | 1 | 1 | 1 | 0 | 181482 | 1 | 1 | 1 | 1 | 1 |
| m.19 | Vitamin D binding protein | 1 | 0 | 1 | 0 | 0 | 181482 | 1 | 1 | 1 | 1 | 1 |
| m.20 | α-1-antitrypsin | 0 | 0 | 0 | 0 | 0 | 6137432 | 1 | 1 | 1 | 1 | 1 |
| m.21 | α-1-antitrypsin | 1 | 1 | 1 | 1 | 0 | 6137432 | 1 | 1 | 1 | 1 | 1 |
| m.22 | Acid α-1-Glycoprotein | 0 | 0 | 0 | 0 | 0 | 112877 | 1 | 1 | 1 | 1 | 1 |
| m.23 | Acid α-1-Glycoprotein | 1 | 0 | 1 | 0 | 0 | 112877 | 1 | 1 | 1 | 1 | 1 |
| m.24 | Haptoglobin | 0 | 0 | 0 | 1 | 0 | 306882 | 1 | 0 | 1 | 1 | 1 |
| m.25 | C3 Component | 0 | 0 | 0 | 0 | 0 | 179965 | 1 | 0 | 1 | 0 | 1 |
| m.26 | Zn-α-2-glycoprotein | 0 | 0 | 1 | 1 | 1 | 38026 | 0 | 0 | 1 | 1 | 1 |
| m.27 | Haptoglobin | 1 | 0 | 1 | 1 | 0 | 306882 | 1 | 0 | 1 | 1 | 1 |
| m.28 | Haptoglobin | 1 | 0 | 1 | 1 | 1 | 306882 | 1 | 0 | 1 | 1 | 1 |
| m.29 | C-reactive | 0 | 0 | 1 | 0 | 0 | 1942435 | 0 | 0 | 1 | 0 | 1 |
| m.30 | Apolipoprotein A-I | 0 | 0 | 0 | 0 | 0 | 90108664 | 1 | 0 | 1 | 1 | 0 |
| m.31 | Apolipoprotein A-I | 1 | 0 | 1 | 1 | 0 | 90108664 | 1 | 0 | 1 | 1 | 0 |
| m.32 | Transthyretin | 0 | 1 | 0 | 1 | 0 | 17942890 | 1 | 1 | 1 | 1 | 1 |
| m.33 | Transthyretin | 0 | 1 | 0 | 1 | 0 | 17942890 | 1 | 1 | 1 | 1 | 1 |

Where:
∩: interception subset;
U: union set;
PM: pneumococcal meningitis;
VM: viral meningitis;
Ctrl: control.

TABLE 6

MATRIX OF THE SPOTS OF THE INTERCEPTION SET OF THE GROUP OF PATIENTS AFFECTED BY VIRAL MENINGITIS

| | | Spots | | | | | | Reviewed after protein identification | | | | |
|---|---|---|---|---|---|---|---|---|---|---|---|---|
| Spot | Proteins | ∩ PM | ∩ VM | U PM | U VM | U Ctrl | gi | ∩ PM | ∩ VM | U PM | U VM | U Ctrl |
| v.1 | not identified | 0 | 0 | 0 | 0 | 0 | — | 0 | 0 | 0 | 0 | 0 |
| v.2 | not identified | 0 | 0 | 0 | 1 | 0 | — | 0 | 0 | 0 | 1 | 0 |
| v.3 | not identified | 0 | 0 | 0 | 0 | 0 | — | 0 | 0 | 0 | 0 | 0 |
| v.4 | not identified | 0 | 0 | 1 | 1 | 1 | — | 0 | 0 | 1 | 1 | 1 |
| v.5 | not named product | 0 | 0 | 1 | 1 | 1 | 22761380 | 0 | 0 | 1 | 1 | 1 |
| v.6 | Hemopexin | 0 | 0 | 1 | 1 | 1 | 386789 | 1 | 1 | 1 | 1 | 1 |
| v.7 | not identified | 0 | 0 | 1 | 1 | 1 | — | 0 | 0 | 1 | 1 | 1 |
| v.8 | Hemopexin | 0 | 0 | 1 | 1 | 0 | 386789 | 1 | 1 | 1 | 1 | 1 |
| v.9 | not named product | 0 | 0 | 1 | 1 | 1 | 22761380 | 0 | 0 | 1 | 1 | 1 |
| v.10 | Transferrin | 0 | 0 | 0 | 1 | 1 | 110590597 | 1 | 1 | 1 | 1 | 1 |
| v.11 | Transferrin | 0 | 0 | 1 | 1 | 1 | 110590597 | 1 | 1 | 1 | 1 | 1 |
| v.12 | Transferrin | 0 | 0 | 1 | 1 | 1 | 110590597 | 1 | 1 | 1 | 1 | 1 |
| v.13 | Transferrin | 0 | 0 | 1 | 1 | 1 | 110590597 | 1 | 1 | 1 | 1 | 1 |
| v.14 | not identified | 0 | 0 | 1 | 1 | 1 | — | 0 | 0 | 1 | 1 | 1 |
| v.15 | Transferrin | 0 | 0 | 1 | 1 | 1 | 110590597 | 1 | 1 | 1 | 1 | 1 |
| v.16 | Transferrin | 0 | 0 | 1 | 0 | 1 | 110590597 | 1 | 1 | 1 | 1 | 1 |
| v.17 | α-1-antitrypsin | 0 | 0 | 0 | 1 | 1 | 177831 | 1 | 1 | 1 | 1 | 1 |
| v.18 | not identified | 0 | 0 | 1 | 0 | 1 | — | 0 | 0 | 0 | 0 | 1 |

TABLE 6-continued

MATRIX OF THE SPOTS OF THE INTERCEPTION SET OF THE GROUP OF PATIENTS AFFECTED BY VIRAL MENINGITIS

|  |  | Spots | | | | | | Reviewed after protein identification | | | | |
|---|---|---|---|---|---|---|---|---|---|---|---|---|
| Spot | Proteins | ∩ PM | ∩ VM | U PM | U VM | U Ctrl | gi | ∩ PM | ∩ VM | U PM | U VM | U Ctrl |
| v.19 | Vitamin D binding protein | 0 | 0 | 1 | 0 | 1 | 181482 | 1 | 1 | 1 | 1 | 1 |
| v.20 | Vitamin D binding protein | 0 | 0 | 1 | 0 | 1 | 181482 | 1 | 1 | 1 | 1 | 1 |
| v.21 | Acid α-1-Glycoprotein | 0 | 0 | 0 | 0 | 1 | 112877 | 1 | 1 | 1 | 1 | 1 |
| v.22 | Transthyretin | 0 | 0 | 1 | 0 | 1 | 17942890 | 1 | 1 | 1 | 1 | 1 |
| v.23 | Transthyretin | 0 | 0 | 0 | 1 | 1 | 17942890 | 1 | 1 | 1 | 1 | 1 |
| v.24 | Prostaglandin D synthase | 0 | 0 | 0 | 0 | 1 | 283806778 | 0 | 0 | 0 | 1 | 1 |
| v.25 | Prostaglandin D synthase | 0 | 0 | 0 | 0 | 0 | 283806778 | 0 | 0 | 0 | 1 | 1 |
| v.26 | not identified | 0 | 0 | 0 | 1 | 0 | — | 0 | 0 | 0 | 1 | 0 |
| v.27 | Transthyretin | 0 | 0 | 0 | 0 | 0 | 17942890 | 1 | 1 | 1 | 1 | 1 |

Where:
∩: interception subset;
U: union set;
PM: pneumococcal meningitis;
VM: viral meningitis;
Ctrl: control.

Example 5

Selection of Candidate Biomarkers for Meningitis Differential Diagnosis

Figure 4:
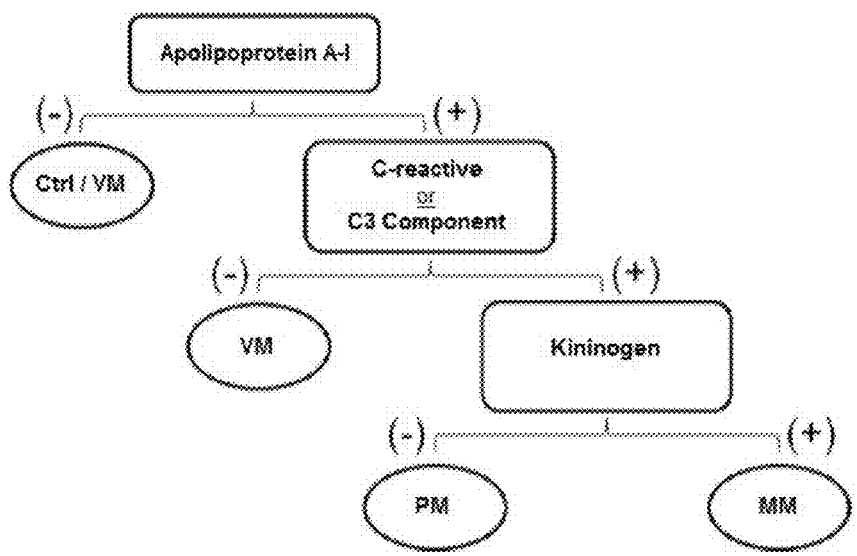
FIG. 4: Qualitative predictive model of meningitis protein biomarkers. The figure depicts the structure of the qualitative predictive model, identifying the employed biomarkers and their three analysis nodes, which represent the sequential form for biomarker detection reading.

Based on the analysis of the matrix (Example 4) of presence versus absence, the four selected proteins were combined to prepare a qualitative predictive method capable of differentiating pneumococcal meningitis from meningococcal meningitis between each other and from viral meningitis or controls (Table 7 and FIG. 4).

TABLE 7

MATRIX OF PRESENCE/ABSENCE OF THE PROTEINS SELECTED FOR THE COMPOSITION OF THE QUALITATIVE PREDICTIVE METHOD

| DESCRIPTION | gi | ∩ PM | ∩ MM | ∩ VM | U PM | U MM | U VM | U Ctrl |
|---|---|---|---|---|---|---|---|---|
| Apolipoprotein AI | 90108664 | 1 | 1 | 0 | 1 | 1 | 1 | 0 |
| C-reactive | 1942435 | 1 | 1 | 0 | 1 | 1 | 0 | 1 |
| C3 Component | 179665 | 1 | 1 | 0 | 1 | 1 | 0 | 0 |
| Kininogen | 4504893 | 0 | 1 | 0 | 0 | 1 | 0 | 0 |

Where:
∩: interception subset;
U: union set;
PM: pneumococcal meningitis;
MM: meningococcal meningitis;
VM: viral meningitis;
CTRL: control.

The absence of apolipoprotein A-I is associated with the absence of infection in the CNS (control group) or viral meningitis. The spots corresponding to apolipoprotein A-I occur in the union set of the group of viral meningitis, but not in the union set of the control group, so that the absence of this protein can indicate any one of these two conditions, and its presence implies the conditions of bacterial or viral meningitis. The spot corresponding to C-reactive protein was identified in the union set of the control group, rather than in the union set of the viral meningitis group. Although alone, the presence of C-reactive protein can indicate the control condition, this can be excluded by the presence of apolipoprotein A-I. Therefore, the C3 component of the complement system or the c-reactive was used, given that the absence of these proteins defines the condition of viral meningitis. Component C3 of the complement system characterizes the condition of bacterial meningitis without defining the etiological agent, wherein its corresponding spot was identified in the interception subsets of the group affected by bacterial meningitis and not in the union set of the group affected by viral meningitis. For the definition of the etiological agent of bacterial meningitis the kininogen protein is proposed. The presence of the kininogen protein is associated with meningococcal meningitis, while its absence indicates pneumococcal meningitis (FIG. 4). Kininogen protein was only found in the interception subset of meningococcal meningitis and its corresponding spot does not belong to the union sets of neither the other meningitis etiologies nor the control group. Based on these results, the predictive method described in FIG. 4 was prepared, in which the presence or absence of the proteins described above must be analyzes sequentially.

Example 6

Prediction of the Cellular Localization of Identified Proteins

Cellular localization of proteins identified by mass spectrometry was predicted by using their respective amino acid sequences obtained in the NCBI database, in the Fasta format. These sequences were inputted in the web version of the software SherLoc 2.

Figure 5:
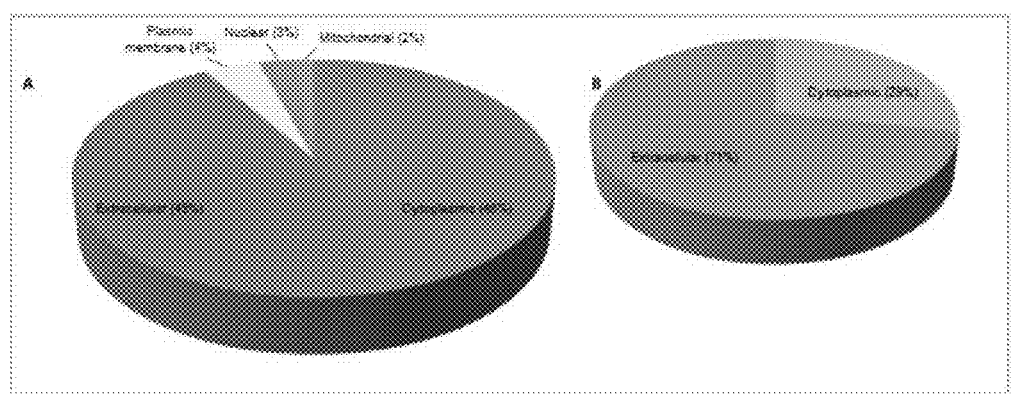
FIG. 5: Prevision of subcellular localization of identified proteins that constitute union sets and intersection subsets of meningitis. A) prediction of the cellular localization of proteins constituting the union sets of meningitis (n=131); B) prediction of the cellular location of proteins constituting the intersection subsets of meningitis (n=37).

The results show that most of the proteins identified in the union sets of meningitis were predicted as cytoplasmic (46%), or extracellular (45%), although they may be also nuclear (3%), of plasmic membrane (4%) or mitochondrial (2%). Furthermore, the identified proteins belonging to the interception subset for meningitis were predicted only as extracellular (71%), or cytoplasmic (29%) (FIG. 5).

One of the most distinct features of eukaryotic cells is the compartmentalization of proteins. The localization of a protein is often an essential step to determine its function.

The occurrence of nuclear and mitochondrial proteins only in the meningitis union sets suggests that it is the case of proteins occasionally released into the extracellular environment due to the death of neurons, glia, or inflammatory cells during the course of meningitis.

The fact that the intersection subsets mainly contain extracellular (and some cytoplasmic) protein reinforces the notion that the proteins evaluated for the selection of meningitis biomarkers participate in the physiological processes of host response to bacterial infection.

Moreover, patients included in this study are from different age groups (infants, children and adults) and their CSF samples were collected along the course of the disease. Another relevant factor of the instant invention is that samples from these patients come from two hospitals of different regions of the country (Southeast and Northeast) and, possibly represent different genetic backgrounds of the host. Thus, every step of the aforementioned experimental design contribute to the reliability of the results found in the instant invention.

The Examples above and on the results generated from the comparative analysis of the CSF proteome of patients affected by pneumococcal, meningococcal, viral meningitis and controls allowed identifying proteins specific of the host response to infection by these pathogens. Specifically, among the identified proteins, four out of these proteins are the subject of the instant invention as biomarkers for the differential diagnosis of malignant and benign meningitis. These biomarker proteins combined in a predictive method were capable of distinguishing patients affected by pneumococcal, meningococcal and viral meningitis from the subjects without infection in the central nervous system. Sensitivity, specificity and accuracy were 100% involving 24 patients (six in each group), tested in duplicate technique.

According to the Example and discussion above, apolipoprotein A-I, C-reactive protein, complement C3 fraction and kininogen were the proteins selected as biomarkers for the differential diagnosis of meningitis, since they were capable of distinguishing patients affected by pneumococcal, meningococcal and viral meningitis from control subjects (subjects without infection or psychiatric or neurodegenerative disease in the central nervous system).

Kits for the differential diagnosis of meningitis in the form of ELISA tests, latex agglutination, Western-blot, side chromatography, capillary electrophoresis, inter alia, are produced from antibodies or aptamers capable of recognizing the biomarkers identified in the instant invention.

The invention claimed is:

1. A predictive method for the differential diagnosis of meningitis comprising the following steps: (a) incubation of the patient's cerebrospinal fluid (CSF) with specific ligands for apolipoprotein A-I biomarkers; C-reactive protein and/or complement C-3 fraction; kininogen; (b) combined detection of apolipoprotein A-I; C-reactive protein and/or complement C-3 fraction; kininogen in the patient's CSF by immunoassay; (c) determination of the results by means of sequential analysis of the first, second and third nodes, wherein: (i) a negative result for apolipoprotein A-I in the first node of the predictive method combined with a negative result for C-reactive protein and/or complement C-3 fraction in the second node of the predictive method; or, positive result for apolipoprotein A-I in the first node of the predictive method combined with a negative result for C-reactive protein and/or complement C-3 fraction in the second node of the predictive method indicates the condition "viral meningitis"; (ii) a positive result for C-reactive protein and/or complement C-3 fraction in the second node of the predictive method combined with a positive result for apolipoprotein A-I in the first node of the predictive method indicates the condition of "bacterial meningitis"; (iii) a positive result for kininogen in the third node of the predictive method combined with positive results for apolipoprotein A-I in the first node and C-reactive protein and/or complement C-3 fraction in the second node of the predictive method indicates the condition of "meningococcal meningitis"; (iv) a negative result for kininogen in the third node of the predictive method combined with positive results for apolipoprotein A-I in the first node and C-reactive protein and/or complement C-3 fraction in the second node of the predictive method indicates the condition of "pneumococcal meningitis".

2. The method according to claim 1, wherein the specific ligands are selected among antibodies or aptamers.

3. The method according to claim 2, wherein the antibodies binding to biomarker proteins are selected among: (i) primary antibodies of the IgG or IgM types with specific affinity against epitopes of each of the four biomarker proteins and produced in rabbits, goats, among other animals; and (ii) secondary antibodies of the IgG type with specific affinity against epitopes of the heavy chains of IgG or IgM from rabbits, goats or other animals, according to the source and type of the primary antibody used.

4. The method according to claim 2, wherein the aptamers binding to biomarker proteins are selected from the group consisting of single-stranded DNA oligonucleotides.

5. In vitro method for the differential diagnosis of meningitis using the predictive method as defined in claim 1, wherein the determination of the presence and the absence of biomarker proteins selected among apolipoprotein A-I, C-reactive protein, complement C3 fraction and kininogen is indicative of disease condition, where (i) a negative result in the first node of the predictive model combined with a negative result in the second node of the predictive model; or, positive result in the first node of the predictive model combined with a negative result in the second node of the predictive model indicates the condition "viral meningitis"; (ii) a positive result in the second node of the predictive model combined with a positive result in the first node of the predictive model indicates the condition of "bacterial meningitis"; (iii) a positive result in the third node of the predictive model combined with a positive result in the first and second nodes of the predictive model indicates the condition of "meningococcal meningitis"; (iv) a negative result in the third node of the predictive model combined with a positive result in the first and second nodes of the predictive model indicates the condition of "pneumococcal meningitis".

6. In vitro method for the differential diagnosis of meningitis using the predictive method as defined in claim 2, wherein the determination of the presence and the absence of biomarker proteins selected among apolipoprotein A-I, C-reactive protein, complement C3 fraction and kininogen is indicative of disease condition, where (i) a negative result in the first node of the predictive model combined with a negative result in the second node of the predictive model; or, positive result in the first node of the predictive model combined with a negative result in the second node of the predictive model indicates the condition "viral meningitis"; (ii) a positive result in the second node of the predictive model combined with a positive result in the first node of the predictive model indicates the condition of "bacterial meningitis"; (iii) a positive result in the third node of the predictive model combined with a positive result in the first and second nodes of the predictive model indicates the condition of "meningococcal meningitis"; (iv) a negative result in the third node of the predictive model combined with a positive result in the first and second nodes of the predictive model indicates the condition of "pneumococcal meningitis".

7. In vitro method for the differential diagnosis of meningitis using the predictive method as defined in claim 3, wherein the determination of the presence and the absence of biomarker proteins selected among apolipoprotein A-I, C-reactive protein, complement C3 fraction and kininogen is indicative of disease condition, where (i) a negative result in the first node of the predictive model combined with a negative result in the second node of the predictive model; or, positive result in the first node of the predictive model combined with a negative result in the second node of the predictive model indicates the condition "viral meningitis"; (ii) a positive result in the second node of the predictive model combined with a positive result in the first node of the predictive model indicates the condition of "bacterial meningitis"; (iii) a positive result in the third node of the predictive model combined with a positive result in the first and second nodes of the predictive model indicates the condition of "meningococcal meningitis"; (iv) a negative result in the third node of the predictive model combined with a positive result in the first and second nodes of the predictive model indicates the condition of "pneumococcal meningitis".

* * * * *